(12) United States Patent
Stettler et al.

(10) Patent No.: US 10,307,357 B2
(45) Date of Patent: Jun. 4, 2019

(54) PREBIOTIC ORAL CARE COMPOSITIONS CONTAINING AN ALKYL GLYCOSIDE

(71) Applicants: COLGATE-PALMOLIVE COMPANY, New York, NY (US); KATHOLIEKE UNIVERSITEIT LEUVEN, Leuven (BE); UNIVERSITEIT GENT, Ghent (BE)

(72) Inventors: Hans Stettler, Hoboken, NJ (US); Wim Teughels, Everberg (BE); Marc Quirynen, Heverlee (BE); Nico Boon, Oosterzele (BE); Gitte Loozen, Borgerhout (BE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/108,111

(22) PCT Filed: Dec. 27, 2013

(86) PCT No.: PCT/US2013/077915
§ 371 (c)(1),
(2) Date: Jun. 24, 2016

(87) PCT Pub. No.: WO2015/099752
PCT Pub. Date: Jul. 2, 2015

(65) Prior Publication Data
US 2016/0338932 A1    Nov. 24, 2016

(51) Int. Cl.
| | | |
|---|---|---|
| *A61K 35/741* | (2015.01) | |
| *A61K 35/74* | (2015.01) | |
| *A61K 8/60* | (2006.01) | |
| *A61Q 11/00* | (2006.01) | |
| *A61K 31/7004* | (2006.01) | |
| *A61K 8/99* | (2017.01) | |

(52) U.S. Cl.
CPC ............. *A61K 8/602* (2013.01); *A61K 8/99* (2013.01); *A61K 31/7004* (2013.01); *A61Q 11/00* (2013.01); *A61K 2800/48* (2013.01)

(58) Field of Classification Search
CPC ............ A61K 2035/115; A61K 35/741; A61K 35/74; A61Q 11/00
See application file for complete search history.

(56) References Cited

U.S. PATENT DOCUMENTS

| | | | |
|---|---|---|---|
| 5,190,746 A | 3/1993 | Cassels et al. | |
| 5,362,480 A * | 11/1994 | Au | A61Q 11/00 424/49 |
| 2005/0079597 A1* | 4/2005 | Chilcott | A61K 31/7004 435/253.4 |
| 2009/0324547 A1* | 12/2009 | Wikstrom | A61K 8/19 424/93.2 |

FOREIGN PATENT DOCUMENTS

| | | |
|---|---|---|
| JP | 2009078982 | 4/2009 |
| JP | 2012140370 | 7/2012 |

OTHER PUBLICATIONS

Kolenbrander et al. Inhibition of Coaggregation between Fusobacterium nucleatum and Porphyromonas (Bacteroides) gingivalis by Lactose and Related Sugars. Injection and Immunity. Oct. 1989. vol. 57. No. 10. pp. 3204-3209.*

E I Weiss et al: "Characterization of lectinlike surface components on Capnocytophaga ochracea ATCC 33596 that mediate coaggregation with gram-positive oral bacteria", Infection and Immunity, May 1, 1987, pp. 1198-1202, http://iai.asm.org/content/55/5/1198. abstract.

* cited by examiner

*Primary Examiner* — Tracy Liu

(57) ABSTRACT

The disclosure relates to an oral care composition an effective amount of at least one C?1-4#191 (optionally hydroxylated) alkyl glycoside, e.g., β-methyl-D-galactoside, wherein the glycoside promotes the growth of beneficial endogenous bacteria and negatively affects the growth of endogenous pathogenic strains of bacteria. The disclosure also relates to methods of use, methods of screening, and methods of manufacture of said oral care compositions.

5 Claims, No Drawings

PREBIOTIC ORAL CARE COMPOSITIONS CONTAINING AN ALKYL GLYCOSIDE

FIELD

The field relates to oral care compositions comprising a prebiotic which is an alkyl glycoside, e.g., a $C_{1-4}$ (optionally hydroxylated)-alkyl glycoside, for example, β-methyl-D-galactoside. The field also relates to methods of using said prebiotic oral care compositions, methods of screening, and methods of manufacture.

BACKGROUND

Different types of sugar are present in our diet and come into contact with plaque during eating. The breakdown of sugars is an important step that influences the plaque environment. Sugar metabolism requires specific enzymes. The genetic disposition and expression of pathway dictates which strains are able to grow on which type of sugars.

The occurrence of high amount of certain sugar may provide a selection advantage to certain species over others, simply due to the fact that they are able to grow on the metabolite but also due to effects that influence the environment such as acid production, bacteriocins, and/or breakdown products that may be metabolized by further species.

When there is an increase in the intake of certain fermentable carbohydrates, this may cause pH to drop in a user's oral cavity. Not only does the acid damage the teeth, but the acidic environment causes a shift toward a more aciduric and acidogenic bacterial, and certain cariogenic bacteria (e.g. *Streptococcus mutans*), which are typically found in relatively small amounts, may actually increase in number and size. Ultimately, this can lead to dental caries. Some species of oral pathogenic bacteria (e.g. *Porphyromonas gingivalis, Tannerella forsythia* and *Aggregatibacter actinomycetemcomitans*) have been implicated in the development of periodontal diseases such as periodontitis, gingivitis, necrotizing periodontitis, necrotizing gingivitis and peri-implantitis. Certain species of oral pathogenic bacteria have been implicated in tooth decay (e.g. *Streptococcus mutans*). Current strategies to address these problems include the use of oral care products containing broad-spectrum antibacterial agents. Such product, however, can inhibit or kill bacteria irrespective of whether the bacteria are beneficial or detrimental. Moreover, pathogens may evolve to develop resistance to antimicrobial agents. Accordingly, alternative methods of prophylaxis and treatment are needed.

"Probiotics" are microorganisms that provide health benefits when consumed. "Prebiotics" are ingestible ingredients that allow specific changes, both in the composition and/or activity in the gastrointestinal microflora that confer benefits upon host well-being and health. While prebiotics are generally known for influencing the composition of the gastrointestinal microflora, there has been little attention directed to using a similar prebiotic strategy to encourage beneficial oral bacteria. Rather than trying to stimulate beneficial bacteria in the mouth, the emphasis has been on avoiding and promptly removing compounds, like sucrose, that encourage harmful oral bacteria.

SUMMARY OF THE INVENTION

We considered that a prebiotic approach, to provide selective stimulation of beneficial bacteria, could provide a valid preventive approach for oral health. Since different bacteria need different substrates in order to grow, providing appropriate substrates could promote growth of beneficial bacterial population, while an increase in beneficial bacteria could result in the suppression of certain pathogenic bacteria. We tested a large number of sugar derivatives to identify substrates that would selectively favor the growth of beneficial bacteria while directly or indirectly suppressing the growth of harmful bacteria.

It is surprisingly found that oral care compositions comprising certain alkyl glycosides (e.g., $C_{1-4}$ (optionally hydroxylated)-alkyl glycoside, for example, β-methyl-D-galactoside) will increase the growth of beneficial bacteria. Such beneficial bacteria include, e.g: *Streptococcus mitis, Streptococcus salivarius, Streptococcus sanguinis, Actinomyces viscosus, Veillonella parvula, Streptococcus gordonii, Capnocytophaga sputigena* and *Actinomyces naeslundii*. It also surprisingly found that the same glycosides that encourage the growth of beneficial bacteria also negatively affect the growth of certain pathogenic strains of bacteria. These pathogenic strains include, e.g.: *Streptococcus mutans, Prevotella intermedia, Porphyromonas gingivalis, Fusobacterium nucleatum, Tannerella forsythia, Aggregatibacter actinomycetemcomitans*, and *Streptococcus sobrinus*.

The present invention contemplates that selective stimulation of beneficial bacteria provides a valid preventive approach for oral health. Without being bound by any theory, it is thought that since bacteria need certain substrates in order to grow, one can obtain certain microbiological shifts in the bacterial environment by selectively encouraging the growth of an individual's beneficial endogenous bacterial population by providing them with appropriate substrates. For example, without being bound by theory, select substrates are preferentially utilized by certain microorganisms. By selecting the appropriate substrate, it is possible encourage the growth of certain microorganisms (e.g., beneficial endogenous bacterial strains) while also directly or indirectly suppressing the growth of select other microorganisms (endogenous pathogenic bacterial strains).

In one aspect, the invention relates to oral care compositions comprising one or more glycosides (e.g., $C_{1-4}$ (optionally hydroxylated)-alkyl glycoside, for example, β-methyl-D-galactoside) useful in a novel prebiotic approach that selectively promotes the growth of beneficial endogenous bacteria but not the growth of harmful bacteria. For example, this may include compositions which promote the growth of at least one of the above-listed beneficial bacteria while not simultaneously promoting growth of any of the above-listed harmful bacteria.

Accordingly, in one aspect the invention provides an oral care composition (Composition 1) comprising an effective amount of at least one $C_{1-4}$ (optionally hydroxylated)-alkyl glycoside, for example, β-methyl-D-galactoside, e.g., an amount effective to promote the growth of beneficial endogenous bacteria in the oral cavity. For example, in various aspects the present invention encompasses:

1.1 Composition 1, wherein the $C_{1-4}$ (optionally hydroxylated)alkyl moiety is $C_{1-4}$ alkyl, e.g., methyl, e.g., wherein the $C_{1-4}$ (optionally hydroxylated)-alkyl glycoside comprises β-$C_{1-4}$ alkyl glycosides, α-$C_{1-4}$ alkyl glycosides, or mixtures thereof.

1.2 Any foregoing composition wherein the $C_{1-4}$ (optionally hydroxylated)alkyl glycoside is a compound that is hydrolyzable by a bacterial glycosidase, e.g., a bacterial β-glycosidase or a bacterial α-glycosidase, for example a bacterial β-galactosidase, to provide the corresponding alkanol and monosaccharide.

1.3 Any foregoing composition wherein the $C_{1-4}$ (optionally hydroxylated)-alkyl glycoside comprises a $\beta$-$C_{1-4}$ alkyl glycoside, e.g., a $\beta$-$C_{1-4}$ alkyl-D-galactoside.

1.4 Any foregoing composition wherein the $C_{1-4}$ (optionally hydroxylated)-alkyl glycoside comprises an $\alpha$-$C_{1-4}$ alkyl glycoside, e.g., a $\alpha$-$C_{1-4}$ alkyl-D-galactoside, e.g., $\alpha$-methyl-D-galactoside.

1.5 Any foregoing composition wherein the glycoside moiety of the $C_{1-4}$ (optionally hydroxylated)-alkyl glycoside is a galactoside.

1.6 Any foregoing composition wherein the $C_{1-4}$ (optionally hydroxylated)alkyl comprises $\beta$-methyl-D-galactoside.

1.7 Any foregoing composition wherein the $C_{1-4}$ (optionally hydroxylated)alkyl comprises $\alpha$-methyl-D-galactoside.

1.8 Any foregoing composition wherein the amount of $C_{1-4}$ (optionally hydroxylated)alkyl glycoside is at least 0.1%, e.g., 0.1% to 5%, e.g., about 0.5%, 1% or 2% by weight of the composition.

1.9 Any foregoing composition wherein the amount of $C_{1-4}$ (optionally hydroxylated)alkyl glycoside is from 1 µmol/ml to 50 µmol/ml, from 2.5 µmol/ml to 35 µmol/ml, from 5 µmol/ml to 25 µmol/ml, from 10 µmol/ml to 25 µmol/ml, from 5 µmol/ml to 20 µmol/ml, about 5 µmol/ml, about 10 µmol/ml, about 20 µmol/ml or about 25 µmol/ml.

1.10 Any foregoing composition wherein the $C_{1-4}$ (optionally hydroxylated)alkyl glycoside is not derived from a plant extract.

1.11 Any foregoing composition wherein the composition promotes the growth in the oral cavity of one or more beneficial endogenous bacterial species, wherein said species are one or more selected from the group consisting of *Streptococcus mitis, Streptococcus salivarius, Streptococcus sanguinis, Actinomyces viscosus, Veillonella parvula, Streptococcus gordonii, Capnocytophaga sputigena* and *Actinomyces naeslundii*.

1.12 Any foregoing composition wherein in the composition promotes the growth of *Streptococcus salivarius*.

1.13 Any foregoing composition, wherein the composition negatively affects the growth in the oral cavity of one or more pathogenic bacterial species, wherein said species are one or more selected from the group consisting of: *Streptococcus mutans, Prevotella intermedia, Porphyromonas gingivalis, Fusobacterium nucleatum, Tannerella forsythia, Aggregatibacter actinomycetemcomitans*, and *Streptococcus sobrinus*.

1.14 Any foregoing composition wherein the composition further comprises at least one species of bacteria that has beneficial effects on oral health.

1.15 Composition 1.14 wherein the species of bacteria that has beneficial effects on oral health is selected from *Streptococcus mitis, Streptococcus salivarius, Streptococcus sanguinis, Actinomyces viscosus, Veillonella parvula, Streptococcus gordonii, Capnocytophaga sputigena, Actinomyces naeslundii* and combinations thereof.

1.16 Any of the preceding compositions further comprising an anti-calculus agent.

1.17 Any of the preceding compositions further comprising an anti-calculus agent which is a polyphosphate, e.g., pyrophosphate, tripolyphosphate, or hexametaphosphate, e.g., in sodium salt form.

1.18 Any of the preceding compositions comprising at least one surfactant selected from sodium lauryl sulfate, cocamidopropyl betaine, and combinations thereof 1.19 Any of the preceding compositions comprising an anionic surfactant, e.g., selected from sodium lauryl sulfate, sodium laureth sulfate, and mixtures thereof 1.20 Any of the preceding compositions comprising sodium lauryl sulfate, in an amount from 0.5-3% by wt of the composition.

1.21 Any of the preceding compositions comprising at least one humectant.

1.22 Any of the preceding compositions comprising at least one humectant selected from glycerin, sorbitol and combinations thereof 1.23 Any of the preceding compositions comprising at least one polymer.

1.24 Any of the preceding compositions comprising at least one polymer selected from polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum), and combinations thereof 1.25 Any of the preceding compositions comprising one or more abrasives, e.g., silica, calcium carbonate, or calcium phosphate abrasives.

1.26 Any of the preceding compositions comprising gum strips or fragments.

1.27 Any of the preceding compositions comprising flavoring, fragrance and/or coloring.

1.28 Any composition obtained or obtainable by combining the ingredients as set forth in any of the preceding compositions.

1.29 Any of the preceding oral care compositions, wherein the composition is a mouthwash, toothpaste, tooth gel, tooth powder, non-abrasive gel, mousse, foam, mouth spray, lozenge, oral tablet, dental implement, or pet care product.

1.30 Any of the preceding compositions wherein the composition is a toothpaste or a mouthwash.

1.31 Any of the preceding compositions wherein the composition is a toothpaste optionally further comprising one or more of one or more of water, abrasives, surfactants, foaming agents, vitamins, polymers, enzymes, humectants, thickeners, preservatives, flavorings, colorings and/or combinations thereof 1.32 Any preceding composition, wherein the composition is a toothpaste further comprising water, abrasive, surfactant, humectant, thickener, and flavoring.

1.33 Any preceding composition wherein the composition is a toothpaste obtained or obtainable by a method of mixing with a toothpaste base, e.g., a toothpaste base comprising one or more of one or more of water, abrasives, surfactants, foaming agents, vitamins, polymers, enzymes, humectants, thickeners, antimicrobial agents, preservatives, flavorings, colorings and/or combinations thereof 1.34 Any preceding composition for use in selectively promoting, in an oral cavity: growth, metabolic activity or colonization of bacteria that have beneficial effects on oral health, relative to growth, metabolic activity or colonization of pathogenic oral bacteria.

1.35 Composition 1.34 wherein the bacteria that have beneficial effects on oral health are selected from *Streptococcus mitis, Streptococcus salivarius, Streptococcus sanguinis, Actinomyces viscosus, Veillonella parvula, Streptococcus gordonii, Capnocytophaga sputigena* and *Actinomyces naeslundii*.

1.36 Composition 1.35 wherein the bacteria that have beneficial effects on oral health are selected from *Actinomyces naeslundii, Actinomyces viscosus* and *Streptococcus salivarius*.
1.37 Composition 1.36 wherein the bacteria that has beneficial effects on oral health is *Streptococcus salivarius*.
1.38 Any of compositions 1.34 to 1.37 wherein the pathogenic oral bacteria are selected from *Streptococcus mutans, Prevotella intermedia, Porphyromonas gingivalis, Fusobacterium nucleatum, Tannerella forsythia, Aggregatibacter actinomycetemcomitans,* and *Streptococcus sobrinus*.
1.39 Any of compositions 1.34 to 1.38, wherein the composition selectively promotes growth, metabolic activity or colonization of bacteria that have beneficial effects on oral health, relative to growth, metabolic activity or colonization of pathogenic oral bacteria, after 24 hours incubation with the bacteria that have beneficial effects on oral health and the pathogenic oral bacteria.
1.40 Any of compositions 1.34 to 1.39, wherein the composition selectively promotes growth, metabolic activity or colonization of bacteria that have beneficial effects on oral health, relative to growth, metabolic activity or colonization of pathogenic oral bacteria, after 48 hours incubation with the bacteria that have beneficial effects on oral health and the pathogenic oral bacteria
1.41 Any preceding composition for use in selectively promoting, in an oral cavity, biofilm formation by bacteria that have beneficial effects on oral health, relative to biofilm formation by pathogenic oral bacteria.
1.42 Composition 1.41 wherein the bacteria that have beneficial effects on oral health are selected from *Streptococcus mitis, Streptococcus salivarius, Streptococcus sanguinis, Actinomyces viscosus, Veillonella parvula, Streptococcus gordonii, Capnocytophaga sputigena* and *Actinomyces naeslundii*.
1.43 Composition 1.42 wherein the bacteria that have beneficial effects on oral health are selected from *Streptococcus salivarius* and *Streptococcus sanguinis*.
1.44 Composition 1.43 wherein the bacteria that has beneficial effects on oral health is *Streptococcus sanguinis*.
1.45 Composition 1.43 wherein the bacteria that has beneficial effects on oral health is *Streptococcus salivarius*.
1.46 Any of compositions 1.41 to 1.45 wherein the pathogenic oral bacteria are selected from *Streptococcus mutans, Prevotella intermedia, Porphyromonas gingivalis, Fusobacterium nucleatum, Tannerella forsythia, Aggregatibacter actinomycetemcomitans* and *Streptococcus sobrinus*.
1.47 Composition 1.46 wherein the pathogenic oral bacteria are selected from *Streptococcus mutans, Prevotella intermedia, Porphyromonas gingivalis, Tannerella forsythia* and *Aggregatibacter actinomycetemcomitans*.
1.48 Composition 1.47 wherein the pathogenic oral bacteria are selected from the group consisting of: *Prevotella intermedia, Porphyromonas gingivalis, Tannerella forsythia* and *Aggregatibacter actinomycetemcomitans*.
1.49 Any preceding composition for use in maintaining and/or re-establishing a healthy oral microbiota.
1.50 Any preceding composition for use in preventing one or more of gingivitis, periodontitis, peri-implantitis, peri-implant mucositis, necrotizing gingivitis, necrotizing periodontitis and caries.

Further provided is a method for prophylaxis or reduction of tooth decay, caries and/or gum disease, comprising contacting the oral cavity with a composition comprising a $C_{1-4}$ (optionally hydroxylated)-alkyl glycoside, for example, β-methyl-D-galactoside), e.g., any of Compositions 1, et seq., e.g by brushing, e.g. on a regular basis over a sufficient period of time to enhance the growth of beneficial bacteria in the oral cavity.

Further provided is a method for increasing the amount of beneficial endogenous bacteria in the oral cavity of a subject in need thereof comprising administering to a subject an oral care composition comprising an effective amount of $C_{1-4}$ (optionally hydroxylated)-alkyl glycoside, for example, β-methyl-D-galactoside), e.g., any of Compositions 1, et seq., e.g., wherein the amount of the $C_{1-4}$ (optionally hydroxylated)alkyl glycoside in the composition promotes the growth of beneficial endogenous bacteria, e.g., wherein the beneficial endogenous bacteria are one or more species selected from the group consisting of *Streptococcus mitis, Streptococcus salivarius, Streptococcus sanguinis, Actinomyces viscosus, Veillonella parvula, Streptococcus gordonii, Capnocytophaga sputigena* and *Actinomyces naeslundii*.

Further provided is a method of selectively promoting, in an oral cavity of a subject: growth, metabolic activity or colonization of bacteria that have beneficial effects on oral health, relative to growth, metabolic activity or colonization of pathogenic oral bacteria; the method comprising contacting the oral cavity with an oral care composition comprising an effective amount of $C_{1-4}$ (optionally hydroxylated)-alkyl glycoside, for example, β-methyl-D-galactoside), e.g., any of Compositions 1, et seq.

Further provided is a method of selectively promoting, in an oral cavity of a subject, biofilm formation by bacteria that have beneficial effects on oral health, relative to biofilm formation by pathogenic oral bacteria; the method comprising contacting the oral cavity with an oral care composition comprising an effective amount of $C_{1-4}$ (optionally hydroxylated)-alkyl glycoside, for example, β-methyl-D-galactoside), e.g., any of Compositions 1, et seq.

Further provided is a method for decreasing the amount of pathological endogenous bacteria in the oral cavity of a subject in need thereof comprising administering to a subject an oral care composition comprising an effective amount of $C_{1-4}$ (optionally hydroxylated)-alkyl glycoside, for example, β-methyl-D-galactoside), e.g., any of Compositions 1, et seq., e.g., wherein the amount of the $C_{1-4}$ (optionally hydroxylated)alkyl glycoside in the composition inhibits the growth of pathological endogenous bacteria, e.g., wherein the pathological endogenous bacteria are one or more species selected from the group consisting of: *Streptococcus mutans, Prevotella intermedia, Porphyromonas gingivalis, Fusobacterium nucleatum, Tannerella forsythia, Aggregatibacter actinomycetemcomitans,* and *Streptococcus sobrinus*.

Further provided is a method of maintaining and/or re-establishing a healthy oral microbiota in a subject, the method comprising contacting an oral cavity of the subject with an oral care composition comprising an effective amount of $C_{1-4}$ (optionally hydroxylated)-alkyl glycoside, for example, β-methyl-D-galactoside), e.g., any of Compositions 1, et seq.

Further provided is a method of preventing one or more of gingivitis, periodontitis, peri-implantitis, peri-implant mucositis, necrotizing gingivitis, necrotizing periodontitis and caries in a subject, the method comprising contacting an oral cavity of the subject with an oral care composition comprising an effective amount of $C_{1-4}$ (optionally hydroxylated)-alkyl glycoside, for example, β-methyl-D-galactoside), e.g., any of Compositions 1, et seq.

In another aspect, the invention relates to methods of screening for compounds that promote the growth of beneficial indigenous bacteria, wherein compositions comprising $C_{1-4}$ (optionally hydroxylated)-alkyl glycoside, for example, β-methyl-D-galactoside) are used as positive controls, wherein screening steps include:

Determining the ability of a first compound (e.g., test compound) to promote the growth of beneficial indigenous bacteria, while simultaneously negatively affects the growth of endogenous pathogenic strains of bacteria;

Determining the ability of a second compound (e.g., control compound) to promote the growth of beneficial indigenous bacteria, while simultaneously negatively affects the growth of endogenous pathogenic strains of bacteria;

Comparing the profile of the first compound with the profile of the second compound;

Selecting a test compound for further testing based upon its ability to affect the growth of beneficial and pathogenic strains of bacteria as compared to the control compound.

In another aspect, the invention relates to methods of screening for compounds that promote the growth of beneficial oral bacteria, wherein screening steps include:

Determining the ability of a first compound (e.g., test compound) to promote the growth of beneficial oral bacteria, while simultaneously negatively affects the growth of pathogenic oral bacteria, e.g., comparing growth of at least one species of beneficial oral bacteria and at least one species of pathogenic oral bacteria, e.g., wherein effect of the first compound on growth is measured by optical density or biofilm formation following at least 24 hours culture in the presence and absence of the first compound;

Optionally determining the ability of a second compound (e.g., control compound) to promote the growth of beneficial bacteria, while simultaneously negatively affecting the growth of pathogenic oral bacteria;

Optionally comparing the profile of the first compound with the profile of the second compound;

Selecting a test compound for further testing based upon its ability to promote the growth of beneficial oral bacteria and inhibit the growth of pathogenic oral bacteria, e.g., as compared to the control compound.

For example, the control compound in the foregoing method of screening may be a $C_{1-4}$ (optionally hydroxylated)-alkyl glycoside, for example, β-methyl-D-galactoside) or a composition comprising a $C_{1-4}$ (optionally hydroxylated)-alkyl glycoside, for example, β-methyl-D-galactoside), e.g., any of Compositions 1, et seq. In some embodiments, the beneficial oral bacteria are one or more species selected from the group consisting of Streptococcus mitis, Streptococcus salivarius, Streptococcus sanguinis, Actinomyces viscosus, Veillonella parvula, Streptococcus gordonii, Capnocytophaga sputigena and Actinomyces naeslundii. In some embodiments, the pathogenic oral bacteria are one or more species selected from the group consisting of: Streptococcus mutans, Prevotella intermedia, Porphyromonas gingivalis, Fusobacterium nucleatum, Tannerella forsythia, Aggregatibacter actinomycetemcomitans, and Streptococcus sobrinus. The invention further provides the use of a compound identified in such a screening method in any of the herein described methods and uses.

Further provided is a use of a $C_{1-4}$ (optionally hydroxylated)-alkyl glycoside, for example, β-methyl-D-galactoside), e.g., as provided in any of the preceding oral care compositions, for prophylaxis or reduction of tooth decay, caries and/or gum disease, or to enhance the growth of beneficial bacteria in the oral cavity, e.g., by contacting the dental surface with a $C_{1-4}$ (optionally hydroxylated)-alkyl glycoside, for example, β-methyl-D-galactoside, e.g., with any of Compositions 1, et seq.

Further provided is a use of $C_{1-4}$ (optionally hydroxylated)-alkyl glycoside, for example, β-methyl-D-galactoside, in the manufacture of an oral care composition, e.g., any of Compositions 1, et seq., for prophylaxis or reduction of tooth decay, caries and/or gum disease, or to enhance the growth of beneficial bacteria in the oral cavity.

In still another aspect, the invention relates to the use of a $C_{1-4}$ (optionally hydroxylated)-alkyl glycoside, for example, β-methyl-D-galactoside, in the manufacture of an oral care product to promote growth of beneficial indigenous (endogenous) bacteria, but not the growth of harmful bacteria.

Further provided is use, in an oral care composition (e.g. any of Composition 1, et seq.) of a $C_{1-4}$ (optionally hydroxylated)-alkyl glycoside, for example, β-methyl-D-galactoside, to:

(a) selectively promote growth, metabolic activity or colonization of bacteria that have beneficial effects on oral health, relative to growth, metabolic activity or colonization of pathogenic oral bacteria;

(b) selectively promote biofilm formation by bacteria that have beneficial effects on oral health, relative to biofilm formation by pathogenic oral bacteria;

(c) maintain and/or re-establish a healthy oral microbiota in a subject; or (d) prevent one or more of gingivitis, periodontitis, peri-implantitis, peri-implant mucositis, necrotizing gingivitis, necrotizing periodontitis and caries in a subject.

DETAILED DESCRIPTION

Unless otherwise indicated, the terms "%" or "percent" when used in connection with an ingredient of the toothpaste compositions of the invention is intended to refer to the percent by weight of the indicated ingredient in the toothpaste composition.

As used herein, "cleaning" generally refers to the removal of contaminants, dirt, impurities, and/or extraneous matter on a target surface. For example, in the context of oral surfaces, where the surface is tooth enamel, the cleaning may remove at least some of a film or stain, such as plaque biofilm, pellicle or tartar.

The terms "indigenous" and "endogenous" are used interchangeably throughout this disclosure.

The term "oral composition" is used herein to designate products which, in the ordinary course of usage, are retained in the oral cavity for a time sufficient to contact substantially all of the dental surfaces but are not intentionally ingested. Such products include, for example, dentifrices such as toothpaste and gels, mouthwashes, chewing gums and lozenges.

The term "glycoside" as used herein refers to a molecule in which a sugar is bound to another functional group via a glycosidic bond. A glycosidic bond is formed between the hemiacetal group of a saccharide (or a molecule derived from a saccharide) and the hydroxyl group of some organic compound such as an alcohol. In particular embodiments, Compositions 1, et seq. comprise a $C_{1-4}$ (optionally hydroxylated)-alkyl glycoside formed between (or hydrolysable to provide) a saccharide and a $C_{1-4}$ (optionally polyhydroxylated)-alkanol. Glycosidic bonds may be classed as α- or β-glycosidic bonds, based on the relative stereochemistry of the anomeric position and the stereocenter furthest from C1 in the saccharide. In some embodiments, Compositions 1, et seq. comprise β-$C_{1-4}$ alkyl glycosides, α-$C_{1-4}$ alkyl glycosides, or mixtures thereof. Hydrolysis of glycosides is catalyzed by a glycosidases, which are typically specific for hydrolysis of either α- or β-glycosidic bonds. In particular embodiments, Compositions 1, et seq. comprise β-$C_{1-4}$ alkyl glycosides hydrolysable by a bacterial β-glycosidase, for example a bacterial β-galactosidase, to provide the bacteria with a metabolizable monosaccharide.

The term "β-methyl-D-galactoside" (also known as methyl-β-D-galactopyranoside) refers to a β-D-galactoside having a methyl substituent at the anomeric position, as depicted in the following structure:

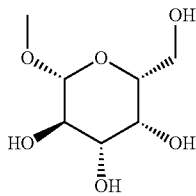

The anomer, α-methyl-D-galactoside (also known as methyl-α-D-galactopyranoside), is also useful in the present invention, e.g., in Compositions 1, et seq., and has the following structure:

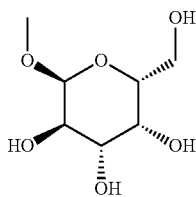

In some embodiments, the oral care compositions disclosed herein, e.g., Composition 1, et seq., comprise water. Water employed in the preparation of the oral care compositions disclosed herein, e.g., Composition 1, et seq., should be deionized and free of organic impurities. Water may make up the balance of the oral care composition. In some embodiments, the oral care compositions disclosed herein, e.g., Composition 1, et seq., comprise 0 to 90 weight % water, e.g., 0.1 to 90 weight % water, e.g., 1 to 80 weight % water, e.g., 2 to 70 weight % water, 5 to 60 weight % water, e.g., 5 to 50 weight % water, e.g., 20 to 60 weight % water, e.g., 10 to 40 weight % water. This amount of water includes the free water that is added plus that amount which is introduced with other components of the oral care composition, such as with sorbitol.

A thickener provides a desirable consistency and/or stabilizes and/or enhances performance (e.g., provides desirable active release characteristics upon use) of the oral care composition. In some embodiments, the oral care compositions disclosed herein, e.g., Composition 1, et seq., comprise from 0.01 to 15 weight % of a thickener, 0.1 to 15 weight % of a thickener, e.g., 0.1 to 10 weight % of a thickener, e.g., 0.1 to 5 weight % of a thickener, e.g., 0.5 to 10 weight % of a thickener, e.g., 0.5 to 5 weight % of at a thickener, e.g., 1 to 4 weight % of a thickener, e.g., 2 to 5 weight % of a thickener, e.g., 2 to 4 weight % of a thickener, e.g., 3 to 4 weight % of a thickener. Higher weight percentages may be used for chewing gums, lozenges and breath mints, sachets, non-abrasive gels and subgingival gels. Thickeners that may be used in the oral care compositions disclosed herein, e.g., Composition 1, et seq., include, for example, carboxyvinyl polymers, carrageenan (also known as carrageenan gum), hydroxyethyl cellulose (HEC), natural and synthetic clays (e.g., Veegum and laponite), water soluble salts of cellulose ethers (e.g., sodium carboxymethylcellulose (CMC) and sodium carboxymethyl hydroxyethyl cellulose), natural gums (e.g., gum karaya, xanthan gum, gum arabic, and gum tragacanth), colloidal magnesium aluminum silicate, silica (e.g., finely divided silica), cross-linked poly(vinyl)pyrrolidone, carbowaxes, fatty acids and salts thereof (e.g., stearic acid and palmitic acid), fatty alcohols (e.g., stearyl alcohol), and mixtures thereof. In some embodiments, a mixture of thickening silica and carrageenan gum is used as the thickener in the oral care compositions disclosed herein, e.g., Composition 1, et seq. In some embodiments, the oral care compositions disclosed herein, e.g., Composition 1, et seq., comprise from 0.01 to 15 weight % of thickening silica and carrageenan gum, 0.1 to 15 weight % of thickening silica and carrageenan gum, e.g., 0.1 to 10 weight % of thickening silica and carrageenan gum, e.g., 0.1 to 5 weight % of thickening silica and carrageenan gum, e.g., 0.5 to 10 weight % of thickening silica and carrageenan gum, e.g., 0.5 to 5 weight % of thickening silica and carrageenan gum, e.g., 1 to 4 weight % of thickening silica and carrageenan gum, e.g., 2 to 5 weight % of thickening silica and carrageenan gum, e.g., 2 to 4 weight % of thickening silica and carrageenan gum, e.g., 3 to 4 weight % of thickening silica and carrageenan gum.

A buffer adjusts the pH of oral care compositions, for example, to a range of about pH 4.0 to about pH 6.0. In some embodiments, the oral care compositions disclosed herein, e.g., Composition 1, et seq., comprise from 0.1 to 10 weight % of a buffer, 0.5 to 10 weight % of a buffer, e.g., 0.5 to 5 weight % of a buffer, e.g., 0.5 to 4 weight % of a buffer, e.g., 0.5 to 3 weight % of a buffer, e.g., 0.5 to 2 weight % of a buffer, e.g., 1 to 2 weight % of a buffer. Buffers that may be used in the oral care compositions disclosed herein, e.g., Composition 1, et seq., include, for example, sodium bicarbonate, sodium phosphate {e.g., monosodium phosphate (NaH2PO4), disodium phosphate (Na2HPO4), trisodium phosphate (Na3PO4)}, sodium hydroxide, sodium carbonate, sodium acid pyrophosphate, citric acid, sodium citrate, and mixtures thereof. In some embodiments, sodium hydroxide is used as the buffer in the oral care compositions disclosed herein, e.g., Composition 1, et seq. In some embodiments, the oral care compositions disclosed herein, e.g., Composition 1, et seq., comprise from 0.1 to 10 weight % of sodium hydroxide, e.g., 0.5 to 10 weight % of sodium hydroxide, e.g., 0.5 to 5 weight % of sodium hydroxide, e.g., 0.5 to 4 weight % of sodium hydroxide, e.g., 0.5 to 3 weight % of sodium hydroxide, e.g., 0.5 to 2 weight % of sodium hydroxide, e.g., 1 to 2 weight % of sodium hydroxide.

A humectant keeps oral care compositions from hardening upon exposure to air. Certain humectants can also impart desirable sweetness or flavor to oral care compositions. In some embodiments, the oral care compositions disclosed herein, e.g., Composition 1, et seq., comprise, on a pure humectant basis, from 0 to 70 weight % of a humectant, e.g., 10 to 70 weight % of a humectant, e.g., 10 to 65 weight % of a humectant, e.g., 10 to 60 weight % of a humectant, e.g., 10 to 50 weight % of a humectant, e.g., 20 to 50 weight % of at a humectant, e.g., 20 to 40 weight % of a humectant. Humectants that may be used in the oral care compositions disclosed herein, e.g., Composition 1, et seq., include, for example, glycerin, sorbitol, xylitol, butylene glycol, polyethylene glycol, propylene glycol, trimethyl glycine, and mixtures thereof. In some embodiments, a mixture of glycerin, sorbitol, and propylene glycol is used as the humectant in the oral care compositions disclosed herein, e.g., Composition 1, et seq. In some embodiments, the oral care compositions disclosed herein, e.g., Composition 1, et seq., comprise, on a pure humectant basis, from 0 to 70 weight % of glycerin, sorbitol, and propylene glycol, e.g., 10 to 70 weight % of glycerin, sorbitol, and propylene glycol, e.g., 10 to 65 weight % of glycerin, sorbitol, and propylene glycol, e.g., 10 to 60 weight % of glycerin, sorbitol, and propylene glycol, e.g., 10 to 50 weight % of glycerin, sorbitol, and propylene glycol, e.g., 20 to 50 weight % of glycerin, sorbitol, and propylene glycol, e.g., 20 to 40 weight % of glycerin, sorbitol, and propylene glycol.

In some embodiments, the oral care compositions disclosed herein, e.g., Composition 1, et seq., comprise a surfactant, e.g., selected from anionic, cationic, zwitterionic, and nonionic surfactants, and mixtures thereof. In some embodiments, the surfactant is reasonably stable throughout a wide pH range. In some embodiments, the oral care compositions disclosed herein, e.g., Composition 1, et seq., comprise from 0.01 to 10 weight % of a surfactant, e.g., 0.05 to 5 weight % of a surfactant, e.g., 0.1 to 10 weight % of a surfactant, e.g., 0.1 to 5 weight % of a surfactant, e.g., 0.1 to 2 weight % of a surfactant, e.g., 0.5 to 2 weight % of a surfactant. In some embodiments, the oral care compositions disclosed herein, e.g., Composition 1, et seq., comprise from 0.01 to 10 weight % of an anionic surfactant, e.g., 0.05 to 5 weight % of an anionic surfactant, e.g., 0.1 to 10 weight % of an anionic surfactant, e.g., 0.1 to 5 weight % of an anionic surfactant, e.g., 0.1 to 2 weight % of an anionic surfactant, e.g., 0.5 to 2 weight % of an anionic surfactant, e.g., 1.5 weight % of an anionic surfactant.

Anionic surfactants that may be used in the oral care compositions disclosed herein, e.g., Composition 1, et seq., include, for example,
  i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
  ii. higher alkyl sulfates, such as sodium lauryl sulfate,
  iii. higher alkyl-ether sulfates, e.g., of formula $CH_3(CH_2)_m CH_2(OCH_2CH_2)_n OSO_3X$, wherein m is 6-16, e.g., 10, n is 1-6, e.g., 2, 3 or 4, and X is Na or K, for example sodium laureth-2 sulfate, $CH_3(CH_2)_{10}CH_2(OCH_2CH_2)_2OSO_3Na$,
  iv. higher alkyl aryl sulfonates such as sodium dodecyl benzene sulfonate (sodium lauryl benzene sulfonate), and
  v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

As used herein, "higher alkyl" refers to C6-30 alkyl.

In some embodiments, the oral care compositions disclosed herein, e.g., Composition 1, et seq., comprise an anionic surfactant. In some embodiments, the anionic surfactant is the water soluble salt of alkyl sulfates having from 10 to 18 carbon atoms in the alkyl radical and water soluble salts of sulfonated monoglycerides of fatty acids having from 10 to 18 carbon atoms. Sodium lauryl sulfate, sodium lauroyl sarcosinate, and sodium coconut monoglyceride sulfonates are examples of anionic surfactants of that type. In some embodiments, the oral care compositions disclosed herein, e.g., Composition 1, et seq., comprise sodium lauryl sulfate, sodium ether lauryl sulfate, or a mixture thereof. In some embodiments, the oral care compositions disclosed herein, e.g., Composition 1, et seq., comprise sodium lauryl sulfate. In some embodiments, the oral care compositions disclosed herein, e.g., Composition 1, et seq., comprise from 0.01 to 10 weight % sodium lauryl sulfate, e.g., 0.05 to 5 weight % sodium lauryl sulfate, e.g., 0.1 to 10 weight % sodium lauryl sulfate, e.g., 0.1 to 5 weight % sodium lauryl sulfate, e.g., 0.1 to 2 weight % sodium lauryl sulfate, e.g., 0.5 to 2 weight % sodium lauryl sulfate, e.g., 1.5 weight % sodium lauryl sulfate.

An abrasive removes debris and surface stains. In some embodiments, the oral care compositions disclosed herein, e.g., Composition 1, et seq., comprise 5 to 70 weight % of an abrasive, e.g., 5 to 60 weight % of an abrasive, e.g., 5 to 50 weight % of an abrasive, e.g., 5 to 40 weight % of an abrasive, e.g., 5 to 30 weight % of an abrasive, e.g., 10 to 30 weight % of an abrasive, e.g., 10 to 20 weight % of an abrasive.

Abrasives that may be used in the oral care compositions disclosed herein, e.g., Composition 1, et seq., include, for example, a calcium phosphate abrasive, e.g., tricalcium phosphate ($Ca_3(PO_4)_2$), hydroxyapatite ($Ca_{10}(PO_4)_6(OH)_2$), dicalcium phosphate dihydrate ($CaHPO_4.2H_2O$, also sometimes referred to herein as DiCal), calcium pyrophosphate, and mixtures thereof. Calcium carbonate, e.g., precipitated calcium carbonate, may also be employed as an abrasive.

Other abrasives that may be used in the oral care compositions disclosed herein, e.g., Composition 1, et seq., include, for example, silica abrasives such as precipitated silicas having a mean particle size of up to about 20 microns, such as Zeodent 115®, marketed by J. M. Huber, as well as sodium metaphosphate, potassium metaphosphate, aluminum silicate, calcined alumina, bentonite or other siliceous materials, or mixtures thereof. Silica abrasives used herein, as well as the other abrasives, may have an average particle size ranging between about 0.1 and about 30 microns, e.g., between about 5 and about 15 microns. The silica abrasives may be from precipitated silica or silica gels, such as silica xerogels. Particular silica xerogels are marketed under the trade name Syloid® by the W. R. Grace & Co. Davison Chemical Division. Precipitated silica materials include those marketed by the J. M. Huber Corp. under the trade name Zeodent®, including the silica carrying the designation Zeodent 115 and 119.

In some embodiments, abrasives that may be used in the oral care compositions disclosed herein, e.g., Composition 1, et seq., include silica gels and precipitated amorphous silica having an oil absorption value of about less than about 100 cc/100 g silica and in the range of about 45 cc/100 g to about 70 cc/100 g silica. Oil absorption values are measured using the ASTA Rub-Out Method D281. In some embodiments, the silica comprises colloidal particles having an average particle size of about 3 microns to about 12 microns, and about 5 to about 10 microns.

In some embodiments, the abrasive comprises a large fraction of very small particles, e.g., having a d50 less than about 5 microns, e.g., small particle silica (SPS) having a d50 of about 3 to abut 4 microns, e.g., Sorbosil AC AC43® (Ineos). Such small particles may be used in formulations targeted at reducing hypersensitivity. The small particle component may be present in combination with a second larger particle abrasive.

Low oil absorption silica abrasives that may be used in the oral care compositions disclosed herein, e.g., Composition 1, et seq., are marketed under the trade designation Sylodent WXA® by Davison Chemical Division of W.R. Grace & Co., Baltimore, Md. 21203. Sylodent 650 XWA®, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive that may be used in the oral care compositions disclosed herein, e.g., Composition 1, et seq.

In some embodiments, the oral care composition disclosed herein, e.g., Composition 1, e.g, 1.1-1.40, comprise a high cleaning silica. In some embodiments, the oral care compositions disclosed herein, e.g., Composition 1, et seq., comprise 5 to 70 weight % high cleaning silica, e.g., 5 to 60 weight % high cleaning silica, e.g., 5 to 50 weight % high cleaning silica, e.g., 5 to 40 weight % high cleaning silica, e.g., 5 to 30 weight % high cleaning silica, e.g., 10 to 30 weight % high cleaning silica, e.g., 10 to 20 weight % high cleaning silica.

In some embodiments, the oral care compositions disclosed herein, e.g., Composition 1, et seq., comprise a sweetener. In some embodiments, the oral care compositions disclosed herein, e.g., Composition 1, et seq., comprise 0.005 to 10 weight % of a sweetener, e.g., 0.01 to 10 weight % of a sweetener, e.g., 0.1 to 10 weight % of a sweetener, e.g., from 0.1 to 5 weight % of a sweetener, e.g., from 0.1 to 3 weight % of a sweetener, e.g., from 0.1 to 1 weight % of a sweetener, e.g., from 0.1 to 0.5 weight % of a sweetener. Sweeteners that may be used in the oral care compositions disclosed herein, e.g., Composition 1, et seq., include, for example, sucrose, glucose, saccharin, sucralose, dextrose, levulose, lactose, mannitol, sorbitol, fructose, maltose, xylitol, saccharin salts (e.g., sodium saccharin), thaumatin, aspartame, D-tryptophan, dihydrochalcones, acesulfame, cyclamate salts, and mixtures thereof. In some embodiments, sodium saccharin is used as the sweetener in the oral care compositions disclosed herein, e.g., Composition 1, et seq. In some embodiments, the oral care compositions disclosed herein, e.g., Composition 1, et seq., comprise 0.005 to 10 weight % sodium saccharin, e.g., 0.01 to 10 weight % sodium saccharin, e.g., 0.1 to 10 weight % sodium saccharin, e.g., from 0.1 to 5 weight % sodium saccharin, e.g., from 0.1 to 3 weight % sodium saccharin, e.g., from 0.1 to 1 weight % sodium saccharin, e.g., from 0.1 to 0.5 weight % sodium saccharin.

In some embodiments, the oral care compositions disclosed herein, e.g., Composition 1, et seq., comprise a flavorant. In some embodiments, the oral care compositions disclosed herein, e.g., Composition 1, et seq., comprise 0.1 to 5 weight % of a flavorant, e.g., 0.1 to 4 weight % of a flavorant, e.g., 0.1 to 3 weight % of a flavorant, e.g., 0.1 to 2 weight % of a flavorant, e.g., 0.5 to 2 weight % of a flavorant, e.g., 0.6 to 2 weight % of a flavorant, e.g., 0.7 to 2 weight % of a flavorant, e.g., 0.8 to 2 weight % of a flavorant e.g., 0.9 to 2 weight % of a flavorant, e.g., 1 to 2 weight % of a flavorant. Flavorants that may be used in the oral care compositions disclosed herein, e.g., Composition 1, et seq., include, for example, essential oils, as well as various flavoring aldehydes, esters, alcohols, and similar materials, as well as menthol, carvone, and anethole, as well as mixtures thereof. Examples of essential oils include oils of spearmint, peppermint, wintergreen, sassafras, clove, sage, eucalyptus, marjoram, cinnamon, lemon, lime, grapefruit, and orange. In some embodiments, a mixture of peppermint oil and spearmint oil is used as the flavorant in the oral care compositions disclosed herein, e.g., Composition 1, et seq.

In some embodiments, the oral care compositions disclosed herein, e.g., Composition 1, et seq., comprise a pigment. In some embodiments, the oral care compositions disclosed herein, e.g., Composition 1, et seq., comprise 0.001 to 20 weight % of a pigment, e.g., 0.01 to 20 weight % of a pigment, e.g., 0.01 to 20 weight % of a pigment, e.g., 0.1 to 20 weight % of a pigment, e.g., 0.1 to 10 weight % of a pigment, e.g., 0.1 to 5 weight % of a pigment, e.g., 0.1 to 3 weight % of a pigment, e.g., 0.1 to 1 weight % of a pigment. In some embodiments, the oral care compositions disclosed herein, e.g., Composition 1, et seq., comprise titanium dioxide. In some embodiments, the oral care compositions disclosed herein, e.g., Composition 1, et seq., comprise 0.001 to 20 weight % titanium dioxide, e.g., 0.01 to 20 weight % titanium dioxide, e.g., 0.01 to 20 weight % titanium dioxide, e.g., 0.1 to 20 weight % titanium dioxide, e.g., 0.1 to 10 weight % titanium dioxide, e.g., 0.1 to 5 weight % titanium dioxide, e.g., 0.1 to 3 weight % titanium dioxide, e.g., 0.1 to 1 weight % titanium dioxide.

In some embodiments, the oral care compositions disclosed herein, e.g., Composition 1, et seq., further comprise an anti-caries agent. In some embodiments, the oral care compositions disclosed herein, e.g., Composition 1, et seq., comprise 0.005 to 10 weight % of the anti-caries agent, e.g., 0.01 to 10 weight % of the anti-caries agent, e.g., 0.01 to 5 weight % of the anti-caries agent, e.g., 0.01 to 1 weight % of the anti-caries agent, e.g., 0.01 to 0.3 weight % of the anti-caries agent, e.g., 0.1 to 10 weight % of the anti-caries agent, e.g., 0.1 to 5 weight % of the anti-caries agent, e.g., 0.1 to 2 weight % of the anti-caries agent, e.g., 0.1 to 1 weight % of the anti-caries agent, e.g., 0.1 to 0.8 weight % of the anti-caries agent, e.g., 0.1 to 0.6 weight % of the anti-caries agent, e.g., 0.1 to 0.5 weight % of the anti-caries agent. In some embodiments, the anti-caries agent is a fluoride ion source. In some embodiments, the oral care compositions disclosed herein, e.g., Composition 1, et seq., further comprise 0.005 to 10 weight % of the anti-caries agent which is a fluoride ion source, e.g., 0.01 to 10 weight % of the anti-caries agent which is a fluoride ion source, e.g., 0.01 to 5 weight % of the anti-caries agent which is a fluoride ion source, e.g., 0.01 to 1 weight % of the anti-caries agent which is a fluoride ion source, e.g., 0.01 to 0.3 weight % of the anti-caries agent which is a fluoride ion source, e.g., 0.1 to 10 weight % of the anti-caries agent which is a fluoride ion source, e.g., 0.1 to 5 weight % of the anti-caries agent which is a fluoride ion source, e.g., 0.1 to 2 weight % of the anti-caries agent which is a fluoride ion source, e.g., 0.1 to 1 weight % of the anti-caries agent which is a fluoride ion source, e.g., 0.1 to 0.8 weight % of the anti-caries agent which is a fluoride ion source, e.g., 0.1 to 0.6 weight % of the anti-caries agent which is a fluoride ion source, e.g., 0.1 to 0.5 weight % of the anti-caries agent which is a fluoride ion source. Examples of fluoride ion sources that may be used in the oral compositions disclosed herein, e.g., Composition 1, et seq., are found in U.S. Pat. No. 3,535,421 to Briner et al.; U.S. Pat. No. 4,885,155 to Parran, Jr. et al., and U.S. Pat. No. 3,678,154 to Widder et al, incorporated herein by reference in their entirety. Other examples of fluoride ion sources include, for example, stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2- ethanol)-dihydro fluoride), ammonium fluoride, titanium fluoride, hexafluorosulfate, and combinations thereof. In certain embodiments the fluoride ion source includes stannous fluoride, sodium fluoride, and sodium monofluorophosphate, as well as mixtures thereof. In some embodiments, the anti-caries agent is sodium fluoride. In some embodiments, the oral care compositions disclosed herein, e.g., Composition 1, et seq., comprise 0.005 to 10 weight % sodium fluoride, e.g., 0.01 to 10 weight % sodium fluoride, e.g., 0.01 to 5 weight % sodium fluoride, e.g., 0.01 to 1 weight % sodium fluoride, e.g., 0.01 to 0.3 weight % sodium fluoride, e.g., 0.1 to 10 weight % sodium fluoride, e.g., 0.1 to 5 weight % sodium fluoride, e.g., 0.1 to 2 weight % sodium fluoride, e.g., 0.1 to 1 weight % sodium fluoride, e.g., 0.1 to 0.8 weight % sodium fluoride, e.g., 0.1 to 0.6 weight % sodium fluoride, e.g., 0.1 to 0.5 weight % sodium fluoride.

In some embodiments, the oral care compositions disclosed herein, e.g., Composition 1, et seq., comprise the anti-caries agent which is a fluoride ion source in an amount sufficient to supply 25 ppm to 25,000 ppm of fluoride ions, e.g., from 100 to 20,000 ppm of fluoride ions, e.g., from 300 to 15,000 ppm of fluoride ions, e.g., from 500 to 10,000 ppm of fluoride ions, e.g., from 500 to 8,000 ppm of fluoride ions, e.g., from 500 to 6,000 ppm of fluoride ions, e.g., from 500 to 4,000 ppm of fluoride ions, e.g., from 500 to 2,000 ppm of fluoride ions, e.g., from 500 to 1,800 ppm of fluoride ions, e.g., from 1000 to 1600 ppm, e.g., 1450 ppm of fluoride ions. The appropriate level of fluoride ions will depend on the particular application. In some embodiments, a toothpaste for consumer use comprises the anti-caries agent which is a fluoride ion source in an amount sufficient to supply from 1,000 to 1,500 ppm of fluoride ions, with pediatric toothpaste having somewhat less. In some embodiments, a dentifrice or coating for professional application comprises the anti-caries agent which is a fluoride ion source in an amount sufficient to supply from 5,000 to 25,000 ppm of fluoride ions.

A whitening agent whitens a tooth to which it is applied. In some embodiments, the oral care compositions disclosed herein, e.g., Composition 1, et seq., comprise a whitening agent. In some embodiments, the oral care compositions disclosed herein, e.g., Composition 1, et seq., comprise a whitening agent in a dental surface-whitening effective amount, e.g., 0.1 to 90 weight % whitening agent, e.g., 0.5 to 50 weight % whitening agent, e.g., 1 to 30 weight % whitening agent, e.g., 2 to 10 weight % whitening agent. Examples of whitening agents that may be used in the oral compositions disclosed herein, e.g., Composition 1, et seq., include, for example, peroxides, metal chlorites, perborates, percarbonates, peroxyacids, hypochlorites, and mixtures thereof. In some embodiments, the whitening agent is hydrogen peroxide or a hydrogen peroxide source, for example, urea peroxide or a peroxide salt or complex (for example, peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or a hydrogen peroxide polymer complex (for example, a peroxide-polyvinyl pyrrolidone polymer complex).

The following examples are further illustrative of the nature of the present invention, but it is understood that the invention is not limited thereto. All amounts and proportions referred to herein and in the appended claims are by weight, unless otherwise indicated.

EXAMPLES

Example 1—Microarray Screen

The metabolic activity of various beneficial oral bacteria and pathogenic oral bacteria in the presence of the glycosides β-methyl-D-galactoside and α-methyl-D-galactoside was investigated.

The beneficial oral bacteria tested were *Streptococcus mitis*, *Streptococcus salivarius*, *Streptococcus sanguinis*, *Actinomyces viscosus*, *Streptococcus gordonii*, *Capnocytophaga sputigena*, *Actinomyces naeslundii* and *Veillonella parvula*. The pathogenic oral bacteria tested were *Streptococcus mutans*, *Prevotella intermedia*, *Porphyromonas gingivalis*, *Fusobacterium nucleatum*, *Tannerella forsythia*, *Aggregatibacter actinomycetemcomitans* and *Streptococcus sobrinus*.

Substrates that were able to increase the metabolic activity of at least one of the above beneficial bacteria while not or only minimally increasing the growth of the pathogenic bacteria are considered to be prebiotic substrates.

The extent of metabolic activity of the tested bacteria in the presence of the above-mentioned glycosides after 24 hours and 48 hours was investigated through a high throughput phenotype microarray system (PM) for microbial cells (Biolog Inc.). Each PM can contain up to 95 different biochemical compounds (e.g. glycosides) that may act as substrates for bacteria as well as one negative control, not containing the substrates. Microarray plates were used in which the different wells of each plate were pre-loaded (by the manufacturer, Biolog Inc.) with different glycosides to be tested. Each bacterial species was tested using a separate microarray plate. Thus, a single bacterial species was tested with a variety of glycosides on each particular plate. The microarrays are based on redox technology, using cell respiration as a universal reporter. Active cell respiration results in the reduction of a tetrazolium dye and in the formation of a strong color—for example, when using the tetrazolium dye "Biolog Redox Dye Mix D", the color changes from transparent/colorless to purple when the dye is reduced. The observation of this color change indicates which of the substrates improve the metabolic activity and health of the cells.

Each bacterial species was collected from blood agar plates (incubated for 48 hours anaerobically at 37° C.) and transferred to an IF-0 Base inoculation fluid (Biolog Inc.), which is a nutritionally poor medium. The resulting cell suspension was adjusted to a transmittance of 42% (relative to the transmittance of the base inoculation fluid with no bacterial species present) at 492 nm using a BioRad SmartSpec 3000 Photometer (the adjustment being effected by adding either further inoculation fluid or further bacteria until the transmittance of 42% was achieved). A 1:5 dilution of this suspension was prepared by mixing 3 mL of the 42% transmittance cell suspension with 15 mL of an inoculation fluid (which inoculation fluid was formed by mixing 11.6 mL sterile water, 62.5 mL IF-0 base inoculation fluid and 0.9 mL of the tetrazolium dye "Biolog Redox Dye mix D"), resulting in a final cell density which was equal to 85% transmittance using a BioRad SmartSpec 3000 Photometer. For each of the glycosides tested, the microarray plate (obtained from the supplier (Biolog Inc.) with glycosides already present in the relevant wells in powder form) was directly inoculated with 100 μL/well of this 85% transmittance cell suspension.

All plates were incubated in an anaerobic atmosphere at 37° C. Color changes were measured spectrophotometrically at 492 nm (Thermo Scientific Multiskan Ascent) at 24 hrs and 48 hrs using the same plate at both time points. For each bacterium tested, a respective control was also used, the control being a well of the plate which contained the particular bacterium (cell suspension) but did not contain any glycosides. After 24 hrs and 48 hrs under continuous shaking in a Multiscan microplate reader, the optical density (OD) of the synthetic medium at 24 hours and 48 hours was measured (using the microplate reader) at a wavelength of 492 nm for each combination of bacterium/glycoside, and for each of their respective controls (i.e. which contained the particular bacterium but no glycosides). For each bacterium, the OD value obtained at 24 hrs and at 48 hrs was divided by the OD value obtained for the respective control at 24 hrs and 48 hrs (respectively), so that the control had a value of 1. A value greater than 1 for a particular combination of bacterium with glycosides therefore indicates that the increase in metabolic activity of the bacteria after 24 hrs or 48 hrs was greater than the increase observed for the control.

The experiment was carried out three times for each combination of bacterium with glycosides, with each repeat being carried out on a different day (thus providing three biological replicas). The controls were also carried out three times, as above. The values shown are the average (mean) of the three single values obtained (as detailed above) for each combination of bacterium with glycosides, at 24 hrs and at 48 hrs. The results are shown in Tables 1 to 4, below:

TABLE 1

Pathogenic bacteria at 24 hrs

|  | A actino** | F nucleatum | P gingivalis | P intermedia | T forsythia | S mutans | S sobrinus |
|---|---|---|---|---|---|---|---|
| β-methyl-D-galactoside | 0.8310 | 0.9051 | 1.1297 | 1.0543 | 1.2183 | 1.1594 | 1.3078 |
| α-methyl-D-galactoside | 0.8204 | 0.8949 | 0.8079 | 0.9609 | 1.0380 | 1.0573 | 1.0761 |

**A actinomycetemcomitans

TABLE 2

Beneficial bacteria at 24 hrs

|  | A naeslundii | C sputigena | S gordonii | A viscosus | S salivarius | S sanguinis | V parvula | S mitis |
|---|---|---|---|---|---|---|---|---|
| β-methyl-D-galactoside | 1.5393 | 1.0421 | 1.4834 | 2.8391 | 6.9837 | 1.0434 | 0.8103 | 1.0977 |
| α-methyl-D-galactoside | 2.1644 | 0.5747 | 0.8960 | 2.4728 | 0.9677 | 1.0198 | 0.9782 | 1.3498 |

TABLE 3

Pathogenic bacteria at 48 hrs

|  | A actino** | F nucleatum | P gingivalis | P intermedia | T forsythia | S mutans | S sobrinus |
|---|---|---|---|---|---|---|---|
| β-methyl-D-galactoside | 0.7733 | 0.7899 | 1.8212 | 1.0046 | 1.8850 | 1.0780 | 1.3002 |
| α-methyl-D-galactoside | 0.7697 | 0.8204 | 0.8180 | 0.9269 | 1.1302 | 0.9904 | 0.9730 |

**A actinomycetemcomitans

TABLE 4

Beneficial bacteria at 48 hrs

|  | A naeslundii | C sputigena | S gordonii | A viscosus | S salivarius | S sanguinis | V parvula | S mitis |
|---|---|---|---|---|---|---|---|---|
| β-methyl-D-galactoside | 1.9886 | 1.0860 | 1.8026 | 3.9827 | 6.4661 | 1.0609 | 0.6840 | 0.9864 |
| α-methyl-D-galactoside | 2.8156 | 0.8435 | 0.8401 | 3.3823 | 0.8829 | 1.1007 | 1.2054 | 1.3555 |

In the above data, a value of 2 was taken as the threshold above which the glycosides caused markedly increased metabolic activity of the bacterium. This value was selected in order to exclude low-stimulating metabolites and avoid false positive results.

As can be seen from the above data, α-methyl-D-galactoside and β-methyl-D-galactoside exhibited prebiotic effects at 24 hrs and at 48 hrs.

Example 2—Twenty-Four Hour Optical Density

The extent of growth of various beneficial oral and pathogenic oral bacteria in the presence of the glycosides β-methyl-D-galactoside and α-methyl-D-galactoside, as examples, was investigated.

The beneficial oral bacteria tested were *Streptococcus mitis, Streptococcus salivarius, Streptococcus sanguinis, Actinomyces viscosus, Streptococcus gordonii, Capnocytophaga sputigena, Actinomyces naeslundii* and *Veillonella parvula*. The pathogenic oral bacteria tested were *Streptococcus mutans, Prevotella intermedia, Porphyromonas gingivalis, Fusobacterium nucleatum, Tannerella forsythia, Aggregatibacter actinomycetemcomitans* and *Streptococcus sobrinus*.

Substrates that were able to increase the growth (or maximal growth density or extent of growth) of at least one of the above beneficial bacteria while not or only minimally increasing the growth (or maximal growth density) of the pathogenic bacteria are considered to be prebiotic compounds.

The extent of growth of the tested bacteria in response to selected glycosides (β-methyl-D-galactoside and α-methyl-D-galactoside) was investigated by setting up growth curves in a nutritionally rich medium (brain heart infusion broth (BHI), Oxoid), over 24 hours. Late exponential growth phase liquid cultures were prepared by transferring the respective bacterium from blood agar plates to BHI and overnight incubation at 37° C. in an anaerobic atmosphere for *A. viscosus, V. parvula, F. nucleatum, P. gingivalis, P. intermedia, T. forsythia, A. naeslundii*, and *C. sputigena*, and in a 5% $CO_2$ environment for *S. salivarius, S. sanguinis, S. mitis, A. actinomycetemcomitans, S. mutans, S. sobrinus* and *S. gordonii*. Overnight cultures were transferred to BHI and adjusted to a concentration of $1 \times 10^7$ CFU/ml (colony forming units per ml) by measuring the optical density at 600 nm ($OD_{600}$) (BioRad SmartSpec 3000). For each strain, 200 µl of the bacterial suspension was added to a 96-well plate containing 20 µl of the respective glycosides. Final concentrations of the glycosides were set to 5, 10, 20 and 25 µmol/ml. For each bacterium tested, a respective control was also used, which did not contain the glycosides. Plates were incubated as previously described.

For each combination of bacterium/glycoside, and for each of their respective controls (i.e. the particular bacterium in the nutritionally rich medium with no glycoside), the optical density was measured at 630 nm ($OD_{630}$) at 0 h and 24 h (Thermo Scientific Multiskan Ascent). Additionally, the $OD_{630}$ for combinations of bacterium/glycosides grown in a 5% $CO_2$ environment were also measured every hour between 0 h and 9 h. For each combination of bacterium/glycoside, the maximal OD value obtained over the 24 hr time period was divided by the maximal OD value obtained for the respective control over the 24 hr period, so that the control had a value of 1. A value greater than 1 for a particular combination of bacterium with glycoside therefore indicates that the extent of bacterial growth over 24 hrs was greater than extent of bacterial growth over 24 hrs for the control.

The experiment was carried out on three different days (thus providing 3 biological replicas) and on each day the experiment was carried out in quadruple (thus providing 4 technical replicas) for each combination of bacterium with glycoside and for each control. For each day and for each combination, the average (mean) of the values obtained (as detailed above) for the four technical replicas was calculated to provide a single value for each combination on each day. The values shown in Tables 5 to 6, below, are the average (mean) of the three single values obtained for each combination of bacterium with glycoside (α-Methyl-D-Galactoside=α-MDG; β-Methyl-D-Galactoside=β-MDG). The results are shown in Tables 5 to 6, below:

TABLE 5

| Pathogenic bacteria over 24 hours | | | | | | | |
|---|---|---|---|---|---|---|---|
| α-MDG 25 µmol/ml | α-MDG 20 µmol/ml | α-MDG 10 µmol/ml | α-MDG 5 µmol/ml | β-MDG 25 µmol/ml | β-MDG 20 µmol/ml | β-MDG 10 µmol/ml | β-MDG 5 µmol/ml |
| | | | | | | | |
| A actino* 0.7395 | 0.7462 | 0.7398 | 0.7382 | 0.7472 | 0.7373 | 0.7723 | 0.7099 |
| F nucleatum 0.7921 | 0.7917 | 0.8398 | 0.8598 | 0.8213 | 0.8161 | 0.8181 | 0.8134 |
| P gingivalis 0.9353 | 0.9132 | 0.9747 | 0.9298 | 0.9364 | 0.9498 | 0.9738 | 0.8852 |
| P intermedia 0.8498 | 0.8637 | 0.9043 | 0.9203 | 0.9102 | 0.9071 | 0.8909 | 0.9000 |
| S mutans 0.2492 | 0.4212 | 0.9003 | 0.9703 | 0.5618 | 0.7929 | 0.9083 | 0.9473 |
| S sobrinus 0.9052 | 0.8858 | 0.8975 | 0.9005 | 0.9111 | 0.9110 | 0.8818 | 0.8914 |
| T forsythia 1.0112 | 0.9846 | 0.9898 | 0.9724 | 1.0042 | 0.9847 | 0.9920 | 0.9652 |

*A actinomycetemcomitans

TABLE 6

| Beneficial bacteria over 24 hours | | | | | | | |
|---|---|---|---|---|---|---|---|
| α-MDG 25 µmol/ml | α-MDG 20 µmol/ml | α-MDG 10 µmol/ml | α-MDG 5 µmol/ml | β-MDG 25 µmol/ml | β-MDG 20 µmol/ml | β-MDG 10 µmol/ml | β-MDG 5 µmol/ml |
| A naeslundii 0.9481 | 0.9595 | 0.9994 | 0.9762 | 0.9802 | 0.9705 | 0.9516 | 0.9746 |
| C sputigena 0.8809 | 0.8728 | 0.8897 | 0.8698 | 0.8575 | 0.8645 | 0.8633 | 0.8841 |
| S gordonii 1.0255 | 1.0089 | 0.9966 | 0.9997 | 1.0054 | 0.9954 | 0.9760 | 0.9811 |

TABLE 6-continued

| | Beneficial bacteria over 24 hours | | | | | | | |
|---|---|---|---|---|---|---|---|---|
| | α-MDG 25 μmol/ml | α-MDG 20 μmol/ml | α-MDG 10 μmol/ml | α-MDG 5 μmol/ml | β-MDG 25 μmol/ml | β-MDG 20 μmol/ml | β-MDG 10 μmol/ml | β-MDG 5 μmol/ml |
| A viscosus | 0.4453 | 0.4433 | 0.5756 | 0.6181 | 0.6464 | 0.6745 | 0.6333 | 0.6467 |
| S salivarius | 0.8725 | 0.8640 | 0.8910 | 0.8965 | 1.7445 | 1.7353 | 1.5208 | 1.2275 |
| S sanguinis | 0.9294 | 0.8872 | 0.9343 | 0.9521 | 0.8842 | 0.8629 | 0.8540 | 0.8787 |
| V parvula | 0.9326 | 0.9141 | 0.9528 | 0.9160 | 0.9462 | 0.9145 | 0.9129 | 0.8912 |
| S mitis | 0.8855 | 0.8843 | 0.9337 | 0.9303 | 0.8116 | 0.9114 | 0.8256 | 0.8435 |

In the above data, a value of 1.25 was taken as the threshold above which the glycoside caused markedly increased extent of growth of the bacterium relative to the control. This value was selected in order to exclude low-stimulating metabolites and avoid false positive results As can be seen from the above data, β-methyl-D-galactoside exhibited prebiotic effects at concentrations of 10, 20 and 25 μmol/ml.

Example 3—Twenty-Four Hour Biofilm Growth

The effects of the test compounds α-methyl-D-galactoside and β-methyl-D-galactoside, as examples, upon biofilm growth of various beneficial oral bacteria and pathogenic oral bacteria is also investigated.

Substrates that were able to increase the biofilm mass of at least one of the above beneficial bacteria while not or only minimally increasing the biofilm mass of the pathogenic bacteria are considered to be prebiotic compounds.

The increase in biofilm formation of the tested bacteria in response to selected glycosides (β-methyl-D-galactoside and α-methyl-D-galactoside) was investigated by setting up biofilm growth assays in a nutritionally rich medium (brain heart infusion broth (BHI), Oxoid), over 24 hours. Late exponential growth phase liquid cultures were prepared by transferring the respective bacterium from blood agar plates to BHI and overnight incubation at 37° C. in an anaerobic atmosphere for A. viscosus, V. parvula, P. gingivalis, P. intermedia, T. forsythia, A. naeslundii, and C. sputigena, and in a 5% $CO_2$ environment for S. salivarius, S. sanguinis, S. mitis, A. actinomycetemcomitans, S. mutans, and S. gordonii. Overnight cultures were transferred to BHI and adjusted to a concentration of $1 \times 10^7$ CFU/ml by measuring the optical density at 600 nm ($OD_{600}$) (BioRad SmartSpec 3000). For each strain, 200 μl of the bacterial suspension was added to a 96-well plate containing 20 μl of the respective glycosides. Final concentrations of the glycosides were set to 5, 10, 20 and 25 μmol/ml. For each bacterium tested, a respective control was also used, which did not contain the glycosides. Additionally, for each bacterium tested, a background control, to correct for background staining, was added. This background control contained the bacterium tested and 0.03 weight % chlorhexidine, as an antiseptic. Plates were incubated as previously described. After 24 hrs the supernatant was removed from the wells of the plates. The wells were washed twice with 1×100 μL PBS (phosphate buffered saline), fixed for 20 minutes with 96% vol. ethanol (96% vol. solution in water) and the biofilm retained at the bottom of the wells was stained with 1 weight % crystal violet (1 weight % solution in water). The bound dye was dissolved with 5% vol. acetic acid (5% vol. solution in water). Quantification of the stained biofilm was performed by measuring the absorbance at 630 nm using a Multiskan Ascent microplate reader (Thermo Scientific).

For each combination of bacterium/glycoside, the OD value obtained at 24 hrs was divided by the OD value obtained for the respective control after subtracting the OD value of the background control, so that the control had a value of 1. A value greater than 1 for a particular combination of bacterium with glycoside therefore indicates that the biofilm growth over 24 hrs was greater than the biofilm growth over 24 hrs for the control.

The experiment was carried out on three different days (thus providing 3 biological replicas) and each day the experiment was carried out in quadruple (thus providing 4 technical replicas) for each combination of bacterium with glycoside and for each control. For each day and for each combination, the average (mean) of the values obtained (as detailed above) for the four technical replicas was calculated to provide a single value for each combination on each day. The values shown in Tables 7 to 8, below, are the average (mean) of the three single values obtained for each combination of bacterium with glycoside. The results are shown in Tables 7 to 8, below:

TABLE 7

| | Pathogenic bacteria at 24 hours | | | | | | | |
|---|---|---|---|---|---|---|---|---|
| | α-MDG 25 μmol/ml | α-MDG 20 μmol/ml | α-MDG 10 μmol/ml | α-MDG 5 μmol/ml | β-MDG 25 μmol/ml | β-MDG 20 μmol/ml | β-MDG 10 μmol/ml | β-MDG 5 μmol/ml |
| A actino* | 1.1720 | 1.1846 | 0.9943 | 0.9911 | 1.0212 | 1.0927 | 1.0188 | 1.1108 |
| P gingivalis | 1.0029 | 0.9820 | 0.9772 | 0.9047 | 0.9163 | 0.9049 | 0.9326 | 0.9407 |
| P intermedia | 0.9774 | 1.0758 | 1.1589 | 1.1518 | 1.1007 | 1.1229 | 1.0925 | 1.1201 |
| S mutans | 1.7240 | 1.5452 | 1.3284 | 1.2046 | 1.2791 | 1.1097 | 1.0007 | 1.3512 |
| T forsythia | 1.0929 | 0.8302 | 1.0506 | 0.7627 | 0.8051 | 0.9049 | 0.6979 | 0.7494 |

*A actinomycetemcomitans

TABLE 8

Beneficial bacteria over 24 hours

| | α-MDG 25 μmol/ml | α-MDG 20 μmol/ml | α-MDG 10 μmol/ml | α-MDG 5 μmol/ml | β-MDG 25 μmol/ml | β-MDG 20 μmol/ml | β-MDG 10 μmol/ml | β-MDG 5 μmol/ml |
|---|---|---|---|---|---|---|---|---|
| A naeslundii | 0.9789 | 0.9692 | 0.9764 | 0.9655 | 0.9727 | 0.9697 | 0.9316 | 0.9907 |
| C sputigena | 0.9669 | 1.1142 | 1.0025 | 0.9689 | 0.9428 | 0.8487 | 0.8100 | 0.7253 |
| S gordonii | 0.6859 | 0.6465 | 0.6458 | 0.6940 | 0.6429 | 0.6763 | 0.6695 | 0.7601 |
| A viscosus | 0.6777 | 0.7490 | 0.7293 | 0.7268 | 0.6322 | 0.6104 | 0.5767 | 0.5917 |
| S salivarius | 0.9258 | 1.1202 | 0.9115 | 0.9165 | 20.1333 | 18.9267 | 5.6484 | 3.1530 |
| S sanguinis | 2.4656 | 2.1593 | 2.4812 | 2.6029 | 2.4211 | 2.3700 | 2.3853 | 1.8586 |
| V parvula | 1.1040 | 1.0577 | 1.0615 | 1.0323 | 1.0384 | 1.0191 | 1.0266 | 1.0106 |
| S mitis | 1.2800 | 1.3917 | 1.2441 | 1.4898 | 1.1692 | 1.1524 | 1.1242 | 1.3127 |

In the above data, a value of 1.6 was taken as the threshold above which the glycoside caused markedly increased biofilm growth of the bacterium relative to the control. This value was selected in order to exclude low-stimulating metabolites and avoid false positive results.

As can be seen from the above data, β-methyl-D-galactoside exhibited prebiotic effects at concentrations of 5, 10, 20 and 25 μmol/ml. α-methyl-D-galactoside exhibited prebiotic effects at concentrations of 5, 10, and 20 μmol/ml.

Example 4—Effects in Mixed Cultures

The pathogenic species *Prevotella intermedia*, *Aggregatibacter actinomyctemcomitans*, *Porphyromonas gingivalis*, *Fusobacterium nucleatum*, *Streptococcus mutans* and beneficial species *Streptococcus salivarius* are used as model organisms for experiments. Bacterial strains are grown on blood agar plates (Oxoid, Basingstoke, UK) supplemented with 5 μg/ml hemin (Sigma Chemical Co, St. Louis, Mo.), 1 μg/ml menadion and 5% sterile horse blood (Biotrading, Keerbergen, Belgium). Bacteria are collected from blood agar plates and transferred to 10 ml brain heart infusion broth (BHI) (Difco Laboratories, Detroit, Mich.). *P. intermedia*, *P. gingivalis*, and *F. nucleatum* were incubated overnight at 37° C. in an anaerobic atmosphere, *A. actinomycetemcomitans*, *S. mutans* and *S. salivarius* are incubated overnight at 37° C. in a 5% CO₂ environment. Bacterial concentration is adjusted by measuring optical density at 600 nm.

In vitro effect of β-methyl-D-galactoside on pathogens: Bacterial solutions of periodontopathogens, *P. intermedia*, *F. nucleatum*, *A. actinomycetemcomitans* and *P. gingivalis*, cariogenic species *S. mutans* and beneficial species, *S. salivarius*, are prepared of which the optical density was adjusted to 1×10⁷ CFU/ml. Experiments are carried out as a dual-species model in 24 well plates containing one pathogen (1 ml) and *S. salivarius* (1 ml). Different conditions are tested: the two microorganisms with (C) or without (D) β-methyl-D-galactoside (200 μl, dissolved in AD (aqua distillata)), only the periodontopathogen with (B) or without (A) β-methyl-D-galactoside (200 μl). β-methyl-D-galactoside is used at a final concentration of 1 mg/ml. When *S. salivarius* is not added to the mixture, BHI is added to obtain an equal volume. When β-methyl-D-galactoside is not added to the mixture, AD was added to obtain an equal volume. Plates are incubated at 37° C. in an anaerobic atmosphere. Selective microbial plating is carried out at 0 h, 24 h, and 48 h. Selective agar plates are prepared for each bacterium. *P. intermedia* and *P. gingivalis* are cultured on CDC anaerobe 5% sheep blood agar (Becton Dickinson, Franklin Lakes, N.J.), *A. actinomycetemcomitans* on Tryptic soy serum bacitracin vancomycin agar (TSBV) (Oxoid, Basingstoke, UK), *F. nucleatum* on crystal violet erythromycin (CVE) agar (Oxoid, Basingstoke, UK), *S. mutans* on tryptone yeast extract cystine sucrose bacitracin (TYCSB) agar (Oxoid, Basingstoke, UK) and *S. salivarius* on Phenylethyl alcohol agar (Becton Dickinson, Franklin Lakes, N.J.).

Statistical analysis: For statistical analysis of the data, the data are $\log_{10}$ transformed to obtain a normal distribution. A linear mixed model is built to assess differences between treatments. A correction for multiple hypothesis testing is carried out.

TABLE 9

In vitro effect of β-methyl-D-galactoside on periodontopathogens in presence and absence of beneficial bacteria (*S. salivarius*)

| A. actinomycetemcomitans | | A | B | C | D |
|---|---|---|---|---|---|
| 0 hours | Average | 5.7633 | 5.7667 | 5.8533 | 6.0000 |
| | Stdev | 0.2673 | 0.2730 | 0.1976 | 0.2858 |
| 24 hours | Average | 7.6600 | 7.8567 | 0.0000 | 8.3067 |
| | Stdev | 0.4051 | 0.2499 | 0.0000 | 0.1102 |
| 48 hours | Average | 4.5500 | 4.4300 | 0.0000 | 7.6300 |
| | Stdev | 0.5679 | 0.1609 | 0.0000 | 0.4590 |

| F. nucleatum | | A | B | C | D |
|---|---|---|---|---|---|
| 0 hours | Average | 5.6000 | 5.6567 | 5.6633 | 5.5833 |
| | Stdev | 0.7608 | 0.7504 | 1.0067 | 0.7935 |
| 24 hours | Average | 7.8300 | 7.7833 | 3.9900 | 7.6467 |
| | Stdev | 1.2650 | 1.4609 | 3.4556 | 1.0498 |
| 48 hours | Average | 8.1033 | 8.0233 | 1.1000 | 7.8433 |
| | Stdev | 0.2150 | 0.5759 | 1.9053 | 0.3262 |

| P gingivalis | | A | B | C | D |
|---|---|---|---|---|---|
| 0 hours | Average | 7.5667 | 7.5233 | 7.5300 | 7.4900 |
| | Stdev | 0.0651 | 0.0306 | 0.0529 | 0.0700 |
| 24 hours | Average | 7.7533 | 7.7100 | 0.0000 | 4.9533 |
| | Stdev | 0.3528 | 0.4651 | 0.0000 | 0.5485 |
| 48 hours | Average | 7.6933 | 7.4900 | 0.0000 | 4.3067 |
| | Stdev | 0.6849 | 0.7019 | 0.0000 | 0.1656 |

| P intermedia | | A | B | C | D |
|---|---|---|---|---|---|
| 0 hours | Average | 6.8933 | 6.9367 | 6.7533 | 6.8167 |
| | Stdev | 0.2804 | 0.3308 | 0.2023 | 0.2892 |
| 24 hours | Average | 8.5600 | 8.6067 | 3.3600 | 5.0400 |
| | Stdev | 0.4521 | 0.2574 | 1.1640 | 1.8293 |
| 48 hours | Average | 8.4067 | 8.2900 | 0.0000 | 8.1467 |
| | Stdev | 0.6545 | 0.7932 | 0.0000 | 0.0651 |

| S. Mutans | | A | B | C | D |
|---|---|---|---|---|---|
| 0 hours | Average | 6.3740 | 6.3342 | 6.3925 | 6.4032 |
| | Stdev | 0.0691 | 0.0620 | 0.0739 | 0.0462 |
| 24 hours | Average | 8.3347 | 8.2372 | 7.5252 | 7.5883 |
| | Stdev | 0.2694 | 0.2702 | 0.2889 | 0.2130 |

TABLE 9-continued

In vitro effect of β-methyl-D-galactoside on periodontopathogens in presence and absence of beneficial bacteria (*S. salivarius*)

| 48 hours | Average | 7.2919 | 7.2128 | 6.7515 | 6.9720 |
|---|---|---|---|---|---|
| | Stdev | 0.0899 | 0.1313 | 0.0704 | 0.2747 |

A: pathogen alone
B: Pathogen + prebiotic
C: Pathogen + prebiotic + *S. salivarius*
D: Pathogen + *S. salivarius*
Data expressed as CFU (colony forming units)/ml
The "average" given here is the mean of three biological replicas.

In vitro dual species competition experiments are set-up to examine the effect of glycosides (e.g. β-methyl-D-galactoside) on the concentration of pathogens in the presence or absence of a beneficial species (*S. salivarius*). A significant decrease ($p<0.001$) in the number of periodontopathogens is observed after 24 h and 48 hours when *S. salivarius* and β-methyl-D-galactoside are added (C) compared with the control containing only *A. actinomycetemcomitans* (A) or only the pathogen and *S. salivarius* (D) or only the pathogen and β-methyl-D-galactoside (B). Best results are achieved with *P. gingivalis* and *A. actinomycetemcomitans* with a decline in concentration to zero after only 24 h. *F. nucleatum* and *P. intermedia* numbers are significantly lower but remained slightly above zero after 48 h. Presence of *S. salivarius* alone does not lead to a significant reduction in the concentration of the periodontopathogens (D) ($p=0.998$) compared with the control containing only the periodontopathogen (A). For *P. gingivalis* a significant reduction is also observed when the pathogen was cultured together with *S. salivarius* without an extra glycoside (β-methyl-D-galactoside) compound ($p<0.001$) compared with the control containing only the pathogen. However as mentioned above, this reduction (D) is significantly lower compared to the conditions containing the glycoside (C). For *S. mutans*, no reduction is observed when β-methyl-D-galactoside and *S. salivarius* are present ($p=0.9999$).

As this experiment shows, if beneficial bacterial growth is supported, the beneficial bacteria can act to inhibit or kill the pathogenic bacteria, thus the prebiotic promotion of beneficial bacteria can help protect the teeth and oral cavity from pathogens, even where the prebiotic alone might support the growth of some pathogens.

Example 6—Compositions Comprising β-Methyl-D-Galactoside

A toothpaste comprising β-methyl-D-galactoside is prepared using the following ingredients:

| Ingredient | % |
|---|---|
| 70% Sorbitol | 20 |
| Glycerin | 20 |
| Water | Q.S. |
| High Cleaning Silica | 10 |
| Gantrez S-97 | 15 |
| Abrasive Silica | 8.8 |
| Thickening Silica | 2.7 |
| Sodium Lauryl Sulfate | 1.5 |
| Sodium Hydroxide | 0-1.2 |
| Sodium CMC - Type 12 | 1.1 |
| Flavor | 1-1.2 |
| Titanium Dioxide | 0.75 |
| Propylene Glycol | 0.5 |
| Carrageenan Gum | 0.48 |
| Sodium Saccharin | 0.3 |
| β-methyl-D-galactoside | 1 |

Another toothpaste comprising β-methyl-D-galactoside is prepared using the following ingredients:

| Ingredient | % |
|---|---|
| 70% Sorbitol | 14 |
| Glycerin | 17 |
| Water | Q.S. |
| High Cleaning Silica | 17 |
| Gantrez S-97 | 17 |
| Thickening Silica | 2.7 |
| Sodium Lauryl Sulfate | 1.5 |
| Sodium Hydroxide | 0-1.2 |
| Sodium CMC - Type 12 | 1.1 |
| Xanthan Gum | 0.8 |
| Flavor | 1-1.2 |
| Titanium Dioxide | 0.5 |
| Propylene Glycol | 0.5 |
| Carrageenan Gum | 0.48 |
| Sodium Saccharin | 0.3 |
| Sodium Fluoride | 0.243 |
| β-methyl-D-galactoside | 0.5 |

The invention claimed is:

1. A method of selectively promoting, in an oral cavity of a subject: growth, metabolic activity or colonization of *Streptococcus salivarius* bacteria that have beneficial effects on oral health; the method comprising contacting the oral cavity with an oral care composition comprising an effective amount of β-methyl-D-galactoside for prebiotic effects of promoting the growth of *Streptococcus salivarius*, wherein the amount of β-methyl-D-galactoside is selected from 10 μmol/ml, 20 μmol/ml, and 25 μmol/ml;
  wherein the composition is a mouthwash, toothpaste, tooth gel, tooth powder, non-abrasive gel, mousse, foam, mouth spray, lozenge, oral tablet, dental implement, or pet care product.

2. The method of claim 1 wherein the amount of β-methyl-D-galactoside is selected from 20 μmol/ml, and 25 μmol/ml.

3. The method of claim 1 wherein the amount of β-methyl-D-galactoside is 20 μmol/ml.

4. The method of claim 1, wherein the composition further comprises bacteria that has beneficial effects on oral health comprising *Streptococcus salivarius*.

5. The method of claim 1, wherein the amount of β-methyl-D-galactoside is 25 μmol/ml.

* * * * *